United States Patent [19]

Manske et al.

[11] 4,353,990
[45] Oct. 12, 1982

[54] SANITATION INDICATOR

[75] Inventors: Wendell J. Manske, Birchwood, Minn.; Paul M. Hawkins, Burlington, Ky.

[73] Assignee: Minnesota Mining and Manufacturing Company, St. Paul, Minn.

[21] Appl. No.: 232,502

[22] Filed: Feb. 9, 1981

[51] Int. Cl.³ .................... C12M 1/00; G01D 21/00; G01K 11/00; C12M 1/34
[52] U.S. Cl. .................... 435/287; 116/207; 116/216; 116/217; 116/219; 422/57; 435/31; 435/291; 435/805; 374/106; 374/160
[58] Field of Search ................ 435/31, 287, 291, 805; 116/207, 216, 217, 219; 73/356, 358; 422/57

[56] References Cited

U.S. PATENT DOCUMENTS

| | | | |
|---|---|---|---|
| 3,055,759 | 9/1962 | Busby et al. | 116/207 |
| 3,362,834 | 1/1968 | Kaye | 116/219 |
| 3,521,489 | 7/1970 | Finkelstein | 73/358 |
| 3,962,920 | 6/1976 | Manske | 116/207 X |
| 3,981,683 | 9/1976 | Larsson et al. | 422/57 |
| 4,134,359 | 1/1979 | Redpath | 116/219 |
| 4,148,272 | 4/1979 | Wetzold | 116/207 X |

*Primary Examiner*—Robert J. Warden
*Attorney, Agent, or Firm*—Cruzan Alexander; Donald M. Sell; Warren R. Bovee

[57] ABSTRACT

A device for monitoring thermal energy input and displaying the relationship of the thermal energy input to a selected time/temperature relationship. The device employs an indicating material which, when melted, expands and flows into a narrow channel to provide an irreversible, visible indication of the thermal energy to which the device has been exposed.

17 Claims, 6 Drawing Figures

SANITATION INDICATOR

FIELD OF THE INVENTION

The present invention relates to thermal energy measurement. More specifically, the present invention relates to a device for monitoring thermal energy input to a sanitizing environment and is particularly useful for accurately monitoring thermal energy input over a short time interval. An inexpensive, simple, disposable device can be constructed according to the present invention to monitor and display a relationship between thermal energy input and a selected time/temperature relationship, such as the thermal death time curve for a selected microorganism.

PRIOR ART

A great number of industrial applications involve the application of heat energy to a particular environment for a particular length of time in order to accomplish a desired result. Sanitation procedures for the destruction of certain microorganisms commonly involve subjecting materials to be sanitized to a controlled environment wherein heat is applied for a required length of time. The times and temperatures employed will vary depending on the sensitivity to temperature of the articles to be sanitized and the resistance of the microorganism to temperature. For example, microorganisms have characteristic thermal death time curves which indicate the lethal temperature/time relationship which prevail and dictate the necessary exposures. Pasteurization conditions are dictated by siuch considerations.

Various techniques have been developed to monitor and indicate the thermal energy input to a particular sterilizing environment. Although electronic monitoring techniques can be employed, the equipment is expensive and is not suited to certain sanitizing activities such as sanitizing dishes and other food-related utensils in mechanical dishwashing equipment.

Conventional thermometers are not useful for this purpose since they do not indicate a time/temperature relationship and provide no irreversible record of the sanitizing activity. Sanitation indicators have been developed which employ indicating compounds having specific melting points. See, for example, U.S. Pat. No. 3,324,723. Other indicators have been developed which rely on a temperature accelerated chemical reaction to cause color change in an indicator. These devices are not useful to accurately reflect the thermal death curve for microorganisms. Yet another device has been described in U.S. Pat. No. 3,981,683, which employs an organic compound having a melting point slightly higher than the sterility temperature to be monitored. The device is constructed to allow steam to diffuse through the device and depress the melting point of the organic compound in order to reflect the contribution of humidity (steam) to the sanitizing conditions.

SUMMARY OF THE INVENTION

The sanitation devices described in the prior art have not provided a satisfactory means of precisely measuring thermal energy input into a particular sanitizing environment and indicating the relationship of the thermal energy input to the thermal death time curve for microorganisms. The present invention provides a simple, reliable device which can be placed in a sanitizing environment and which will accurately monitor and display the thermal energy input to such environment. In addition, the device can be constructed to accurately indicate the relationship of the thermal energy input to the thermal death time curve for selected microorganisms.

The energy monitors of the present invention comprise an indicating material having a selected melting point which, when melted, expands. The expansion of this indicating material is monitored to provide an irreversible indication of the thermal energy input to which the device has been exposed. A display means is provided to indicate the relationship of the thermal energy input to the energy level sufficient to kill selected microorganisms. In a preferred embodiment, the device comprises a body member and at least one fixed-volume reservoir cavity in the body member. The device further includes a display means remote from the reservoir cavity. The device has a fixed-volume flow channel connecting the reservoir cavity and the display means, the dimensions of the flow channel being such as to allow passage of liquid therethrough. The reservoir cavity is completely filled with a solid indicating material which is capable of changing to an expanded, liquid phase at a selected elevated temperature. Thus, the volume of the indicating material is a function of temperature. The quantity of indicating material and the expansion properties of the material must be such as to completely fill the reservoir cavity and flow channel when in the liquid state. The device also includes means for relieving pressure generated by expansion of the indicating material.

When such a device is maintained above a given temperature threshold, the solid indicating material melts and expands into said flow channel. When the device has been above the temperature threshold for the requisite period of time, the indicating material will have flowed into the display means. Thus, the device is capable of monitoring thermal energy input and displaying the relationship of said input to a given time-temperature relationship, such as the thermal death curve for selected microorganisms. The device can be used to monitor the performance of sanitation and pasteurization equipment to ensure that sanitation cycles are effective, e.g., reach threshold kill temperatures, without being wasteful of energy by operating at temperatures greatly in excess of those required.

While the sanitation indicators of the present invention are described herein as being useful to monitor the sanitation cycles of commercial hot water dishwashers, these indicators can also be useful in monitoring various other heating cycles. Typical examples of such use are the monitoring of the pasteurization cycles for beverages such as milk, wine, beer and fruit juices as well as the sterilization cycles for medical devices and even the laundering cycle for clothing and other fabrics.

THE DRAWING

DETAILED DESCRIPTION OF THE PREFERRED EMBODIMENTS

Figure 1:
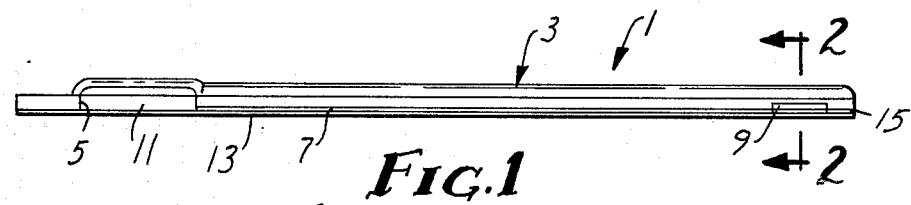
FIG. 1 is a side view of a device according to the present invention.

Referring to the Drawing, FIG. 1, shows a side elevation of an indicator device 1. The device comprises body member 3 in which there is disposed a recessed cavity 5 connected via a recessed flow channel 7 to display means 9. Cover means 13 is attached to body member 3 and covers reservoir cavity 5 and flow channel 7 such that said cavities have a fixed volume. Indicating material 11 is shown completely filling cavity 5. Sorbent pad 9 functions as a display means and is accessible by indicating material 11 through flow channel 7. Pressure relief passage 15 communicates with flow channel 7 and the atmosphere.

Body member 3 can be made of a wide variety of materials. Materials in which the necessary recesses and cavities can be drilled, milled, etched, cut, or otherwise formed, such as by molding techniques, can be usefully employed in the present invention. The materials may be organic or inorganic. Metals, such as aluminum, copper, etc. can be used, however, plastic materials, such as organic polymeric materials are generally preferred. The materials should be transparent or otherwise provided with windows or other means so that movement of the indicating material into the display means can be observed. In addition, the material should be able to retain the necessary physical properties, e.g., dimensional stability, at temperatures which would be expected to be encountered during storage and use. Polycarbonate, cellulose acetate butyrate and other transparent polymeric materials are particularly preferred for use as body members in the present invention.

The channels and other cavities can be made to precisely controlled dimensions by normal injection molding techniques when the preferred plastic materials are employed.

The covering material, 13, can be a thin, flexible material which can be adhered to body member 3. Cover material 13 should be strong enough so that it is not deformed when the indicator material 11 melts and expands. However, cover material 13 must be sufficiently formable so that it can be pressed into intimate contact with indicating material 11 at the time of manufacturing the device as shall be described in greater detail hereinafter. The material employed as the cover material 13 should be thermally conductive in order to rapidly transmit thermal energy to the indicating material 11 from the surrounding environment and to prevent solidification of the indicating material 11 as it proceeds toward sorbent pad 9. Thus, the cover material should function as a "thermal window" responsively coupling the indicating material 11 to the surrounding environment. A particularly preferred material is aluminum foil, preferably a foil having dead-soft temper. Such foils can be provided with an adhesive backing resistant to water, heat and the like, so that they can be adhered to, and remain in intimate contact with, body member 3.

Sorbent pad 9 can be any material which will readily sorb indicating material 11. A paper pad is suitable. However, it has been found that when the sanitation indicator is to be used in a wet environment it is preferable that the sorbent pad 9 be fully oleophilic. As such, it will readily sorb indicator material 11, but will resist absorption of any water which may enter the indicator through relief passage 15. A particularly useful material is available commercially under the trade name "TYVEK" from E. I. Du Pont De Nemours, Inc.

Indicating material 11 can be a material which will melt at a selected elevated temperature (i.e., a temperature above room temperature) and which, when melted, will expand a sufficient amount to fill cavity 5, flow channel 7 and contact sorbent pad 9.

Figure 6:
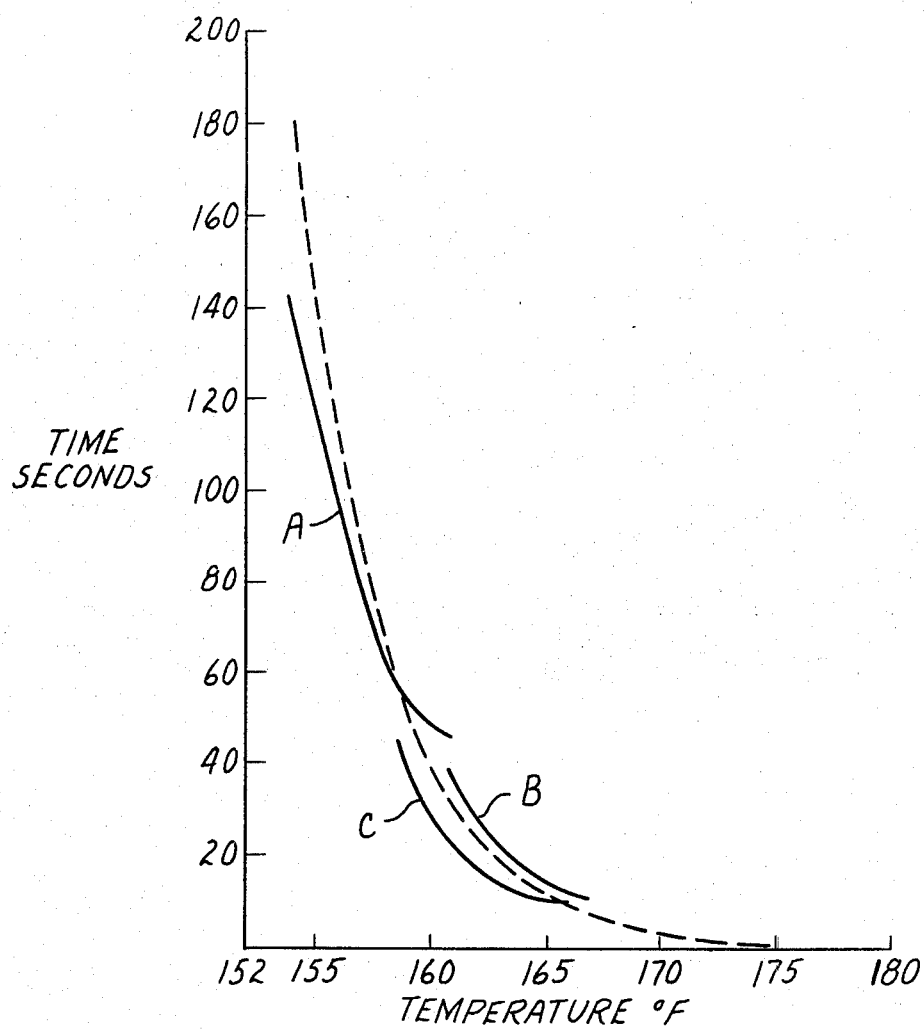
FIG. 6 is a graph showing the minimum time/temperature curve specified for commercial dishwashers to ensure adequate sanitation (dashed line). The solid lines show the time/temperature relationships measured by various sanitation indicators prepared according to the present invention.

Materials having the requisite melting and expansion properties can be prepared from readily available materials which are known in the art. For example, U.S. Pat. Nos. 3,631,721 and 4,170,956 disclose organic materials which can be formulated to melt at selected temperature ranges and which expand when melted. Exemplary of compositions useful in the present invention is a mixture of, by weight, 96 parts N-octyl myristamide, 4 parts N-octyl lauramide and 0.2 parts Spirit Soluble Fast 3 B Dye (BASF Wyandotte Corp.). This composition has a melting point of about 66°–67° C., a specific heat of 0.58 calories per centigrade degree per gram at 90° C. and a coefficient of thermal expansion on changing from solid to liquid of 0.0759. A second representative compound comprises, by weight, 77.5 parts N-dodecyl lauramide, 22.5 parts N-octyl lauramide and 0.3 part Spirit Soluble Fast HFL Dye (BASF Wyandotte Corp.). This composition has a melting point of 69°–70° C., a specific heat of 0.59 calories per centigrade degree per gram at 90° C. A composition comprising, by weight, 76 parts N-dodecyl lauramide, 24 parts N-Octyl lauramide and 0.3 part Spirit Soluble Fast HFL Dye has a melting point of about 69° C. The time/temperature properties of indicators using the above three compositions are shown in FIG. 6 as Curves A, B and C, respectively. The melting points noted above were determined using a capillary melting point apparatus heating at the rate of 1° C. per 30 seconds.

Dye is generally added to the above compositions to make them more visible in the sorbent display pad.

Figure 4:
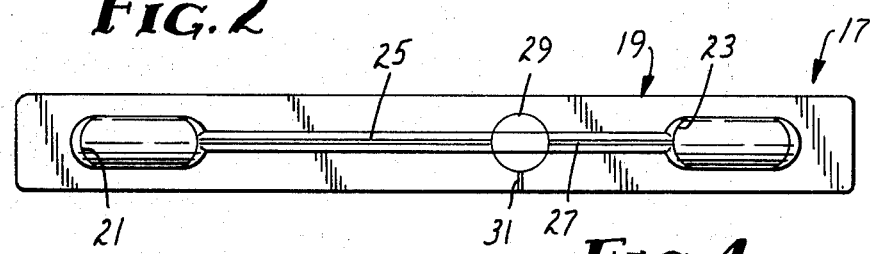
FIG. 4 is a top view of an indicating device according to the present invention having two separate reservoir cavities.
Figure 5:
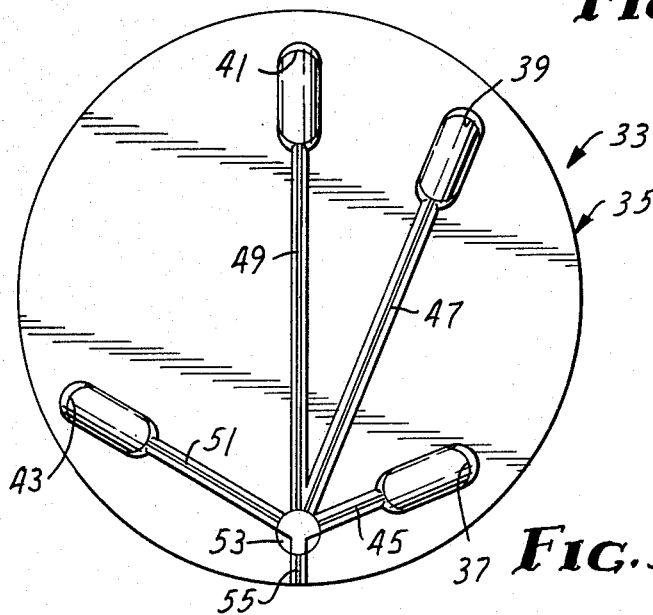
FIG. 5 is yet another embodiment of the device of the present invention having multiple reservoir cavities.

FIGS. 4 and 5 of the Drawing show alternate embodiments of the present invention which have the capability of containing 2 or more different indicating materials. Such devices are capable of displaying the relationship of thermal energy input in a particular environment to multiple time-temperature relationships. Sanitation indicator 17 comprises body member 19 including a first cavity 21, a second cavity 23 and first and second flow channels 25 and 27, respectively. Sorbent pad 29 functions as a display element and pressure relief passage 31 vents flow channels 25 and 27 to the atmosphere.

Cavities 21 and 23 can be filled with different indicating materials (not shown) having different melting points. For example, reservoir cavity 21 could be filled with an indicating material having a melting point which is lower than the melting of the second indicating material in cavity 23. Since flow channel 25 is longer than flow channel 27, the device will monitor and display the effect of a first temperature for a given period of time and a second, higher, temperature for a relatively shorter period of time.

FIG. 5 shows a sanitation indicator 33 comprising a circular body member 35 which includes multiple reservoir cavities 37, 39, 41 and 43. These cavities are connected to sorbent pad 53 by flow channels 45, 47, 49 and 51 having various lengths. Pressure relief passage 55 vents the flow channels to the atmosphere. Indicating materials (not shown) having the same or different melting points could be provided in each of the various reservoir cavities to provide a device capable of monitoring and indicating various heat histories.

The devices of the present invention find particular utility in monitoring hot water sanitation conditions, such as a dishwashing cycle. Heating cycles for appliances such as dishwashers can be established by determining the time/temperature conditions required to destroy selected microorganisms which are found in such environments.

The concept of "cumulative heat factor" has been accepted in the public health field as related to *Mycobacterium tuberculosis* in the pasteurization of milk. Studies using *Mycobacterium phlei* in water have now established that a similar relationship exists with regard to sanitization conditions in dishwashers. Further, the cumulative effects of time and temperature have been studied and the heat unit equivalent (HUE) required to sanitize dishes, etc., has been firmly established.

The concept of heat unit equivalents is based on the finding that 1800 seconds at 143° F. (62° C.) is suficient to kill *Mycobacterium tuberculosis* in milk or *Mycrobacterium phlei* in water. 1 second at 143° F. (62° C.) provides 1 HUE. Similarly, it has been found that only 15 seconds at 161° F. (71° C.) will kill the microorganism. Thus, one second at 161° F. (71° C.) provides 1800/15=120 HUE's. In like manner, the HUE's for each temperature can be established. To determine the total HUE's produced in a heat cycle the average temperature for each second is determined and the HUE's calculated for that second. The sum of the HUE's can be determined for the total cycle.

A further discussion of pasteurization, sterilization and concepts relating to thermobacteriology in food processing can be found in Block, Seymour S., "Disinfection, Sterilization and Preservation," 2nd Edition, Lea and Febiger, Philadelphia (1977), and in Stumbo, C. R., "Thermobacteriology in Food Processing," 2nd Edition, Academic Press, New York (1973).

A cycle producing 3600 HUE's has been adopted by the National Sanitation Foundation as the minimum sanitation requirement for commercial hot water dishwashers. This provides a safety factor of two. Such an HUE curve is shown as a dashed line in FIG. 6 of the Drawing.

Sanitation devices, such as institutional dishwashing machines, must be capable of cleaning the dishes and providing, as a minimum sanitization cycle, thermal energy input corresponding to some point on the curve shown in FIG. 6. Exceeding this thermal input insures that microorganisms which may be present on the dishes will be destroyed. However, it is not desirable to exceed this thermal energy input by a substantial amount, since to do so merely wastes energy without providing any beneficial effect.

The devices of the present invention can be inexpensively constructed to faithfully monitor the thermal energy input for a dishwashing cycle and display the relationship of the input to the thermal death curve shown in FIG. 6. This allows the use of minimum amounts of energy while still providing an appropriate safety factor. This is accomplished by balancing the thermal capacity and heat transfer characteristics of the device as well as the melting point and expansion coefficient of the indicating material. In practice, such a balance is favorably struck by employing a body member of polycarbonate and an aluminum foil cover. The thermal conductivity of the polycarbonate is about 0.11 btu/hr ft² °F./ft whereas thwe thermal conductivity for aluminum is in excess of 100 btu/hr ft²°F./ft. Thus, the aluminum foil cover acts as a thermal window transferring heat directly and quickly to the indicating material. This provides a device which is responsive to temperature cycles of relatively short duration e.g. 5 minutes or less.

The fine tuning of the device is accomplished by blending various organic materials having the desired melting points and expansion coefficients to closely approximate the selected thermal curve.

The present invention can be further illustrated by reference to the following example.

EXAMPLE 1

Figure 3:
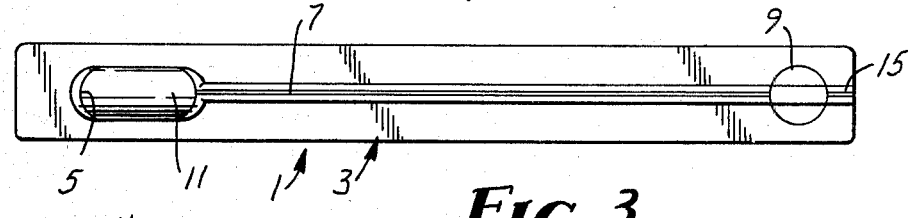
FIG. 3 is a top view of the device shown in FIG. 1.
Figure 2:
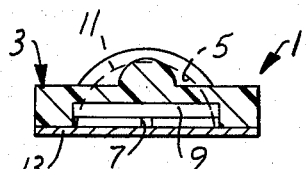
FIG. 2 is a section view along line 2—2 of FIG. 1.

A sanitation indicator according to the present invention can be prepared as follows:

A plastic body member was injection molded from polycarbonate to have a structure similar to that shown in FIGS. 1-3 of the Drawing. The nominal length of the body member was about 9 cms while the nominal width and thickness of the body member were 1 cm and 0.25 cms respectively. The channel 7 connecting the reservoir cavity 5 and the display means 9 was 0.025 inches (0.521 mm) deep, 0.006 inches (0.52 mm) wide and 2.34 inches (59.4 mm) long. It has been found that the channel should not be made much wider than 0.15 mm so that the foil cover will not be pressed into and plug the channel.

An indicating material was prepared by combining 96 parts by weight n-octyl myristamide and 4 parts by weight n-octyl lauramide. A dye (BASF Spirit Soluble Fast 3 B) was added in the amount of 0.2 parts by weight. This composition had a melting point of about 66°-67° C. The mixture was melted at 110° C. and mixed thoroughly for one hour. After separating any particulate residue, the reservoir cavity in the body member was filled with about 0.05 gram of indicating material using a preheated eye dropper. Due to the surface tension of the indicating material the reservoir cavity can be filled to provide a convex-shaped charge without causing the indicating material to run out of the cavity.

The indicating material was allowed to cool and solidify and was then buffed flush with the surface of the plastic body member by rubbing with a sheet of smooth bond paper. Following buffing, the surface of the indicator material was examined and any visible voids were filled with additional melted indicator material and the surface rebuffed. Following buffing, the flow channel and other cavities in the body member were cleaned using a blast of compressed air.

A display disc comprising a sorbent pad (Tyvek, DuPont) was adhered in the cavity at the other end of the flow channel with a polyvinylacetate adhesive. The display disc was located so as to be directly adjacent the flow channel outlet.

The reservoir cavity, flow channel, display pad cavity, and pressure relief passage were then covered by applying an aluminum foil tape having a pressure-sensitive adhesive backing (3M tape #425) to the back of the plastic body member. The tape was applied with slight pressure and then trimmed to size with a razor blade. Care must be taken to avoid plugging the pressure relief passage. A body member was then placed into a support device and the aluminum foil tape firmly pressed down using a smooth metal plate in a platen press at a press pressure of 5600 psi ($3.9 \times 10^7$ Pascals). Following this first pressing, the foil tape was again pressed at 1280 psi ($8.8 \times 10^6$ Pascals) using a pressing plate having an elastomeric projecting portion corresponding in shape to the reservoir cavity. The elastomeric portion was about 0.075 inches (1.9 mm) thick and was recessed into the metal plate so only about 15 mils (0.38 mm) protruded above the metal plate. The elastomeric material had a Shore A Durometer hardness of about 76. The particular elastomeric material chosen was a Fluorel rubber. When the pressed plate was pressed down over the body member, the elastomeric portion caused the aluminum foil tape to be intimately pressed into contact with the solidified indicating material in the reservoir cavity.

Following pressing, the entire indicator was exposed to a 63°-64° C. environment for about 8 hours to condition the adhesive backing on the tape, i.e., to convert any unstable adhesive to a more stable form which will not react with or otherwise affect the indicating material.

The indicator prepared as described above exhibited a run-out time (i.e. the time required for the first color to appear on the display pad) of 55-70 seconds in a stirred water bath at 70 plus or minus 0.1° C. with water flowing past the indicator at a rate of 0.65 feet/sec. (19.8 cm/sec). The time/temperature characteristics of this indicator are shown as curve "A" in FIG. 6. This curve closely approximates the sanitation curve (dashed line) which is acceptable as the standard. Thus, this device can be used to monitor the sanitation cycle in a dish washing machine. For example, the device is placed on a dish in a machine and the machine run through the sanitation cycle. If the required amounts of thermal energy has reached the dish the display portion of the indicator will register this condition. If insufficient heat has been applied the indicator material will not have reached the display area. The machine can then be adjusted to provide the necessary thermal input.

For short time, high temperature cycles indicating materials comprising 77.5 parts n-dodecyl lauramide and 22.5 parts n-octyl lauramide or 76 parts n-dodecyl lauramide and 24 parts n-octyl lauramide may be used to more closely approximate the lower portion of the dashed curve in FIG. 6. These compositions provide indicators having the time/temperature characteristics shown in curves B and C, respectively, of FIG. 6.

What is claimed is:

1. A device for monitoring and irreversibly displaying short term thermal energy input as a function of a selected time-temperature relationship, said device comprising, in combination:
   (a) a dimensionally stable body member,
   (b) at least one-fixed volume reservoir cavity, in said body means,
   (c) a display means comprising a liquid-sorbent pad located remote from said reservoir cavity,
   (d) a fixed-volume flow channel connecting each of said reservoir cavities and said display means, the dimensions of said flow channel being such as to allow passage of said liquid therethrough,
   (e) solid indicating material completely filling each of said reservoir cavities, said solid indicating material capable of changing to an expanded liquid phase at selected elevated temperatures, the volume of said indicating material being a function of temperature, the quantity of said indicating material in each flow cavity being sufficient to completely fill the reservoir cavity and connecting flow channel when in the liquid state,
   (f) means for relieving pressure generated by expansion of the indicating material, and
   (g) means covering said reservoir, flow channel and display means for rapidly conducting thermal energy from the surrounding environment to the indicating material, whereby when said device is exposed to said selected elevated temperature said solid indicating material melts, expands into said flow channel and into said display means in response to and as a function of the thermal energy input.

2. A device according to claim 1 wherein said indicating material is an organic composition which is solid at room temperature.

3. A device according to claim 1 wherein the indicating material has thermal properties such that the device displays a time-temperature relationship corresponding to a thermal death time curve for a microorganism.

4. A device according to claim 3 wherein said microorganism is *Mycobacterium tuberculosis* or *Mycobacterium phlei*.

5. A device according to claim 4 wherein said indicating material is an organic composition comprising one or more organic compounds selected from the group consisting of n-octyl myristamide and n-octyl lauramide.

6. A device according to claim 5 wherein said indicating material comprises a dye soluble in said indicating material.

7. A device according to claim 1 wherein said body member comprises a transparent polymeric material.

8. A device according to claim 7 wherein said polymeric material is selected from the group consisting of cellulose acetate butyrate and polycarbonate polymers.

9. A device according to claim 1 wherein said liquid sorbent material is an oleophilic pad.

10. A device for detecting and displaying thermal energy input and displaying the relationship of said input to a preselected time-temperature relationship, said device comprising in combination:
   (a) a thin, elongated, transparent plastic body member, having first and second ends, and first and second sides, said first side being substantially planar,
   (b) a first recess in said first side proximate said first end of said body member,
   (c) a second recess in said first side of said body member and remote from said first recess,
   (d) a flow channel in said first side of said body member connecting said first and second recesses,
   (e) said first recess completely filled with a solid indicating material which is capable of changing to an expanded liquid phase at elevated temperature, the volume of said indicating material being a function of temperature, said indicating material containing a colored dye.
   (f) a pad in said second recess capable of sorbing said colored indicating liquid, said pad being in communication with said flow channel,
   (g) a pressure relief channel in said first side of said body member connecting said second recess to the edge of said body member, and
   (h) a thermally conductive cover means attached to the first side of said body member and covering said first recess to form a completely filled, fixed-volume reservoir cavity and covering said flow channel to form a fixed-volume flow channel, said cover means further covering said second recess and said pressure relief channel,
whereby when said device is exposed to said elevated temperature said solid indicating material melts, expands into said flow channel and into said display means in response to and as a function of the thermal energy input.

11. A device according to claim 10 wherein the indicating material has thermal properties such that the device displays a time-temperature relationship corresponding to a thermal death curve for a microorganism.

12. A device according to claim 11 wherein said microorganism is *Mycobacterium tuberculosis* or *Mycobacterium phlei*.

13. A device according to claim 12 wherein said indicating material comprises one or more compounds selected from the group consisting of n-octyl myristamide and n-octyl lauramide.

14. A device according to claim 10 wherein said cover means is a metal foil.

15. A device according to claim 14 wherein said metal foil is dead soft aluminum foil.

16. A device according to claim 10 additionally comprising a third recess in said first side of said body member and remote from said first recess, a flow channel in said first side of said body member connecting said second and third recesses, said third recess completely filled with a second, solid indicating material which is capable of changing to an expanded liquid phase at an elevated temperature different from said first solid indicating material in said first recess, the volume of said second indicating material being a function of temperature, said second indicating material containing a colored dye and wherein said cover means covers said third recess and said connecting flow channel.

17. A device according to claim 16 wherein said dye in said second indicating material is a different color from the dye in said first indicating material.

* * * * *